United States Patent [19]

Nofre et al.

[11] Patent Number: 4,645,678

[45] Date of Patent: Feb. 24, 1987

[54] SWEETENING AGENTS

[75] Inventors: Claude Nofre, Lyons; Jean-Marie Tinti, Meyzieu, both of France

[73] Assignee: Universite Claude Bernard - Lyon 1, France

[21] Appl. No.: 532,499

[22] Filed: Sep. 15, 1983

[30] Foreign Application Priority Data

Sep. 17, 1982 [FR] France .................. 82 15832

[51] Int. Cl.[4] .................. A23L 1/236; C07C 149/43; C07C 147/13; C07C 127/00
[52] U.S. Cl. .................. 426/548; 560/16; 560/34; 560/9; 560/13; 562/426; 562/439; 562/430; 424/48; 558/413; 558/418
[58] Field of Search .................. 424/48; 260/112.5 R; 426/548; 562/439, 426, 430; 560/16, 34, 13, 9; 558/413, 418

[56] References Cited

U.S. PATENT DOCUMENTS

| | | | |
|---|---|---|---|
| 3,492,131 | 1/1970 | Schlatter | 260/548 |
| 3,642,491 | 2/1972 | Schlatter | 426/548 |
| 3,714,139 | 1/1973 | Schlatter | 260/112.5 R |
| 3,800,046 | 3/1974 | Schlatter | 426/548 |

FOREIGN PATENT DOCUMENTS 1027113 2/1978 Canada .
0048051 of 0000 European Pat. Off. .

OTHER PUBLICATIONS

J. M. Tinti et al., *Naturwissenschaften*, 68, 143–145 (1981).
J. M. Tini et al., *Naturwissenschaften*, 67, 193–194 (1980).
J. W. Tsang, *J. Med. Chem.*, 27, 1663–1668 (1984).
Ariyashi et al., *Bulletin of the Chemical Society of Japan*, 47 (2), 326–330 (1974).

*Primary Examiner*—Nicky Chan
*Assistant Examiner*—F. T. Moezie
*Attorney, Agent, or Firm*—Parkhurst & Oliff

[57] ABSTRACT

Compounds of the formula:

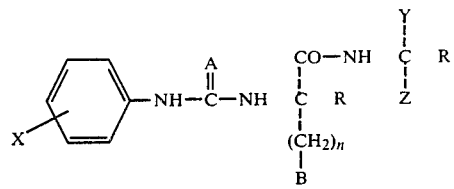

in which:
X represents at least one lone-electron pair donor group;
A represents an oxygen or a sulfur atom, or an optionally substituted imino or methylene group;
R represents a hydrogen atom or an alkyl group of 1 to 4 carbon atoms;
n represents a number equal to zero or to one;
B represents a COOH or COOM group (M designating a cation);
Y represents either a lone-electron pair donor group, or an alkyl group R' of 1 to 4 carbon atoms;
Z represents
either an optionally substituted hydrophobic group R", R" designating an alkyl, cycloalkyl or aryl group of 1 to 12 carbon atoms;
or a lone-electron pair donor group on which a hydrophobic group R" is fixed;
are useful as sweetening agents.

10 Claims, No Drawings

SWEETENING AGENTS

This invention relates to novel compounds useful as sweetening agents. It also relates to the use of those compounds to sweeten foodstuffs, beverages, cosmetics, pharmaceuticals, etc. And in still another aspect, it relates to sweetening compositions containing those compounds.

As is known, "sweetening agents", also called "sweeteners", are compounds capable of communicating their sweet taste to various food or pharmaceutical products with which they are mixed. The use of synthetic sweeteners may be envisaged as a substitute for sucrose in low-sugar diets for diabetics and in low-calorie diets for obese persons, by reason of their low calorie content. In certain countries, the use of sweeteners is not limited solely to dietetic or pharmaceutical needs and their use in ordinary foodstuffs has given this type of compound considerable importance. However, the compounds most widely consumed at the present time, namely sodium cyclamate and saccharin, apart from their aftertaste (bitter aftertaste for saccharin), have had questions raised as to their potential carcinogenic effect and the use thereof has been prohibited or subjected to a control, depending on the country concerned.

French Pat. No. 1,577,545, corresponding to U.S. Pat. Nos. 3,492,131, 3,714,139, 3,642,491, and 3,800,046, describes a synthetic sweetener known under the generic name of aspartame, of which the sweetening power lies between that of sodium cyclamate and that of saccharin. However, this product presents the particular drawback of being expensive, capable of bringing about a dietary excess of L-phenylalanine and of being unstable, particularly by degrading into a diketopiperazinic derivative. One possible means for avoiding this cyclization into diketopiperazine is the substitution of the α-amino group of L-aspartic acid.

Up to the present time, few compounds derived from aspartame and possessing the substituted α-amino group have proved to be sweet (cf. for example European Pat. No. 0 048 051). However, these compounds have a sweetening power identical to that of aspartame and therefore remain expensive products which can also bring about an excess of L-phenylalanine in the diet.

The present invention overcomes these drawbacks. In fact, the compounds according to the invention present the advantage of having the α-amino group of L-aspartic acid substituted and, unlike the previously described products, possess an extremely high sweetening power much greater than that of aspartame, which is totally unexpected. For example, this sweetening power may be up to 300 times greater than that of aspartame, which considerably reduces the cost of using this sweetening agent and reduces to a negligible quantity the L-phenylalanine consumed.

These novel chemical products are characterized in that they comprise a compound of general formula (I):

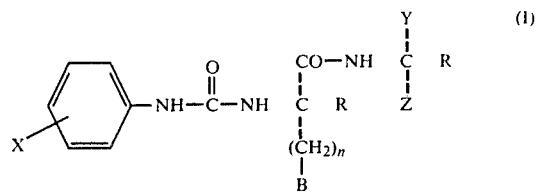

in which:

X represents at least one lone-electron pair donor group;

A represents an oxygen or a sulfur atom, or an optionally substituted imino or methylene group;

R represents a hydrogen atom or an alkyl group of 1 to 4 carbon atoms;

n represents a number equal to zero or to one;

B represents a COOH or COOM group (M designating a cation);

Y represents either a lone-electron pair donor group, or an alkyl group R' of 1 to 4 carbon atoms;

Z represents:
either an optionally substituted hydrophobic group R", R" designating an alkyl, cycloalkyl or aryl group of 1 to 12 carbon atoms;
or a lone-electron pair donor group on which a hydrophobic group R" is fixed.

As is known, a "lone-electron pair donor group" is a group of which at least one atom is a carrier of one or more pairs of unshared electrons capable of interacting via hydrogen bonds, and a "hydrophobic group" is a nonpolar or slightly polar group.

The invention relates also to new synthetic sweeteners reproducing the general formula (I) above.

Advantageously, in the compounds according to the invention:

X is selected from the group constituted by the CN, COOR, $SO_2R'$, SOR', COR', $NO_2$, halogen, $CH_2CF_3$, $CF_2CF_3$, $SO_3H$, $SO_2NRR$, CONRR, $OSO_2R'$, $CH_2OR$ groups;

A is selected from the group constituted by an oxygen or a sulfur atom;

R is an hydrogen atom;

n is equal to one;

B is a COOH or COOM group, M being a cation selected from the group $Na^+$, $K^+$, $NH_4^+$, $Ca^{2+}$, $Mg^{2+}$, $Li^+$;

Y is selected from the group constituted either by the COOR', $CH_2OR$, $CHOHCH_3$, $CONHCH_2CH_2OH$, CONHCHRCOOR', $CONHCHRCONH_2$, $CF_3$, $CCl_3$ groups, or by a R' group;

Z is a hydrophobic group selected from the group constituted:
either by a $CH_2C_6H_5$ (benzyl), $CH_2C_6H_{11}$ (cyclohexylmethyl), $C_6H_5$ (phenyl), $C_6H_{11}$ (cyclohexyl), $C_5H_{11}$ (pentyl), iso-$C_5H_{11}$ (isopentyl), $C_4H_9$ (butyl), iso-$C_4H_9$ (isobutyl) group, these groups being able to be diversely substituted, like for example $CH_2C_6H_4OR$, $(CH_2)_xOR$, $(CH_2)_xSR'$, $(CH_2)_xCOOR'$, $(CH_2)_xSO_2R'$, $(CH_2)_xO$-COR', with x being equal to 0, 1 or 2;

or by amides (CONHR", CONR"R", CONHCHR'-'COOR', $CONHCHR"CONH_2$), carboxylic esters (COOR"), halogen derivatives (such as for example $CF_2R"$), alcohols (such as CHOHR" for example).

In practice:

X is in 4 position and is selected from the group constituted by the CN, COOCH$_3$, COOC$_2$H$_5$, SO$_2$CH$_3$, COCH$_3$ groups;

R is an hydrogen atom;

n is equal to one;

Y is selected from the group constituted by the groups COOCH$_3$ or CH$_3$;

Z is selected from the group constituted by the CH$_2$C$_6$H$_5$ (benzyl), CH$_2$C$_6$H$_{11}$ (cyclohexylmethyl), C$_6$H$_5$ (phenyl), C$_6$H$_{11}$ (cyclohexyl), C$_5$H$_{11}$ (pentyl), iso-C$_5$H$_{11}$ (isopentyl), CONHCH$_2$CH$_2$CH$_3$ (propylamide), CONHCH(CH$_3$)$_2$ (isopropylamide), CONHCH(C$_3$H$_5$)$_2$ (dicyclopropylcarbinylamide), CONHCH(C$_3$H$_5$)C(CH$_3$)$_3$ (t-butylcyclopropylcarbinylamide).

The preferred sweetening compounds of the invention are essentially:

derivatives of N-(4-X-phenylcarbamoyl or 4-X-phenylthiocarbamoyl)-L-aspartyl-L-phenylalanine methyl ester of the following general formula:

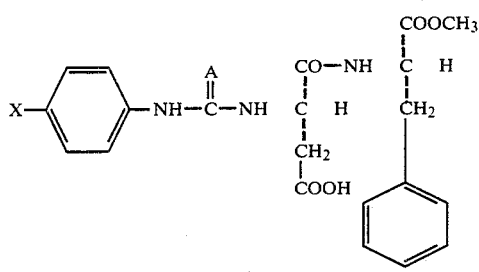

derivatives of N-(4-X-phenylcarbamoyl or 4-X-phenylthiocarbamoyl)-L-aspartyl-L-1-(1-Z)ethanamine:

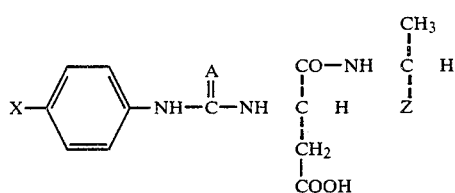

derivatives of N-(4-X-phenylcarbamoyl or 4-X-phenylthiocarbamoyl)-L-aspartyl-D-alaninamide:

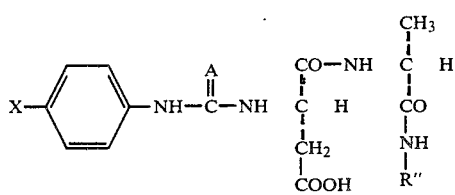

The compounds according to the invention may be prepared by condensation between the compounds of general formulae II and III:

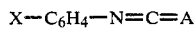

$$X-C_6H_4-N=C=A \qquad (II)$$

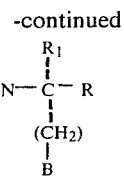

with the groups X, A, R, n, and B as defined hereinabove and with the group R$_1$ representing either a group

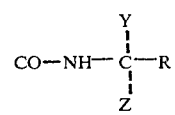

(with Y and Z defined as hereinabove) or a COOH group.

The reaction between the compounds of general formulas II and III may be suitably carried out in water at room temperature. Compound II may be previously dissolved in a solvent such as benzene, chlorobenzene, methanol or ethanol, which makes it possible considerably to improve the yield of the reaction.

Where R$_1$ is the group

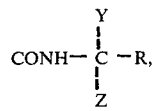

compound III then presents the following general formula:

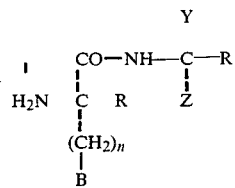

After condensation with compound II, the compound of general formula I is then directly obtained.

Where R$_1$ is the group COOH, compound II is therefore brought into contact with the compound of general formula IV:

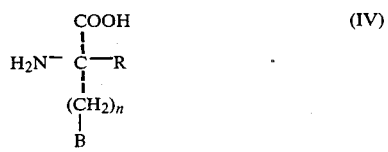

in which B may be either the free carboxyl group, or a previously protected carboxyl group in the form for example of a benzyl or t-butyl ester. In the same way, compound V of general formula:

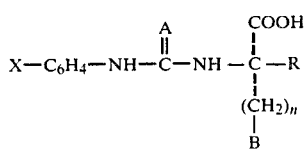

is then obtained.

This compound is then brought into contact with compound (VI) of general formula:

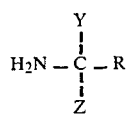

in which Y, Z and R are such as defined hereinabove. The reaction is effected in the presence of an appropriate dehydrating agent, of which particular mention may be made of the alkoxyacetylenes, carbodiimides with, in particular, dicyclohexylcarbodiimide, or isoxazolium salts. This reaction between compounds V and VI may also be carried out by activating the free α-carboxyl group or the amino group of the two compounds. The activation of the free carboxyl group of compound V, which is preferably used, is carried out by various methods of which particular mention may be made of those employing the synthesis of an intermediary: mixed anhydride, acid chloride, azide or activated ester (such as for example an ester of p-nitrophenol or of N-hydroxysuccinimide).

Activation via a mixed anhydride formed in situ from an alkyl chloroformate (such as ethyl or methyl chloroformate) is one of the preferred methods. The mixed anhydride is obtained by addition of triethylamine, then of alkyl chloroformate to a solution of compound V in tetrahydrofuran or dimethylformamide.

This reaction may be carried out at between $-20°$ C. and $+25°$ C. The mixed anhydride is rapidly formed (a few minutes at $-10°$ C.) and compound VI may then be added. After a few hours, compound I is directly obtained after the conventional treatments, consisting in particular in a washing by acid and basic solutions.

In the particular case of the group B of compound V being a protected carboxyl group in the form, for example, of a benzyl or t-butyl ester, deblocking of this protector group is necessary to obtain compound I with the free carboxyl group.

In this way, the benzyl ester protector group is eliminated by hydrogenolysis which is the choice method for eliminating this group. The reaction may be appropriately carried out in a solvent such as methanol, ethanol or 70% acetic acid, in the presence of catalyst such as palladium on active charcoal (10%) under low hydrogen pressure and at room temperature. In the case of a protector group of the t-butyl ester type, it is suitably eliminated by an acid hydrolysis which may be rapidly carried out with a solution of hydrogen bromide or of hydrogen chloride in glacial acetic acid or with anhydrous trifluoroacetic acid. Compound I is finally obtained in which the group B represents a free carboxyl group.

It is possible to obtain the compounds of the invention differently, particularly when B is a free carboxyl group and n is equal to 1.

In this case, the diacid corresponding to the following general formula:

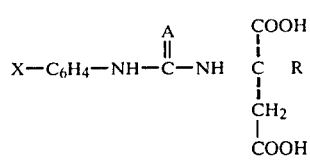

is converted into an anhydride of general formula VII by action of a suitable dehydration agent, such as for example acetic anhydride or trifluoroacetic anhydride.

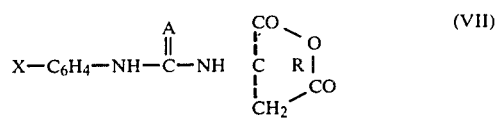

This reaction may be suitably carried out by heating the diacid, in the presence of the chosen anhydride, to reflux for some minutes. The presence of a solvent such as benzene, chloroform or tetrahydrofuran does not prove indispensable for this reaction. Compound VII thus obtained is placed in presence with compound VI dissolved in an inert solvent, such as dimethoxyethane, tetrahydrofuran or ethyl acetate. This reaction directly leads to corresponding compound I.

These sweetener compounds could be used for any application of the sweetener in order to sweeten any human or animal foods or drinks, by addition of these sweetener products in appropriate effective quantity. "Effective quantity" means the quantity which could be detected by the physiologic senses of a human.

Since the sweetness of these compounds is so intense, they are conveniently used admixed with a bulking agent or carrier, for example, partially hydrolyzed starch products (dextrins) or other consumable but substantially non-metabolizable starch or cellulose derivative or other low calorie carbohydrate composition. Such bulking agents and carriers are mixed with the sweetener compounds of the present invention by dry blending, spray drying, etc., and packaged as free-flowing powders or compressed into tablets as is well known in the art of making compositions intended for sweetening tea, coffee, breakfast cereals, grapefruit and other comestibles commonly sweetened with sugar.

The sweetener compounds of the present invention can also be used in combination with other sweetening agents, natural agents, such as sugar, or synthetic agents, such as saccharin or aspartame.

The invention will be more readily understood on reading the following examples given by way of non-limiting example.

EXAMPLE 1

Synthesis of
N-(4-cyanophenylcarbamoyl)-L-aspartyl-L-alanine
methyl ester (compound No. 12 of Table I)

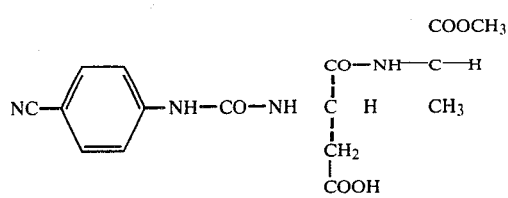

Step 1

Preparation of N-(4-cyanophenylcarbamoyl)-L-apartic acid β-benzyl ester 3 g (13.4 mmol) of L-aspartic acid β-benzyl ester are dissolved in 40 cm³ of water, then a concentrated solution of sodium carbonate is added until a basic pH ($\cong$9–10) is obtained. 2.2 g (15.2 mmol) of 4-cyanophenyl isocyanate dissolved in 10 cm³ of benzene are then added.

The solution is vigorously stirred for 2 hours at 20° C. before filtration and extraction with 4×15 cm³ of ethyl ether. The aqueous phase is then acidified up to pH=1 by hydrochloric acid then extracted with 4×50 cm³ of ethyl acetate. After drying over anhydrous sodium sulfate and concentration, 4.5 g of an oily product which crystallizes rapidly are obtained (yield 93%). The solid has a melting point of 145°–147° C.

Step 2

Preparation of
N-(4-cyanophenylcarbamoyl)-β-benzyl-ester-L-aspartyl-L-alanine methyl ester 1.2 g (3.3 mmol) of N-(4-cyanophenylcarbamoyl)-L-aspartic acid β-benzyl ester previously obtained are dissolved in 20 cm³ of dimethoxyethane. The solution is cooled to −10° C. before the addition of 0.33 g (3.3 mmol) of triethylamine, then of 0.36 g (3.3 mmol) of ethyl chloroformate. The mixture is stirred for five minutes at the temperature of −10° C. before the addition of 0.41 g of L-alanine methyl ester.

Stirring is then maintained for 5 minutes at −10° C., then for 12 hours at room temperature. After filtration and washing of the precipitate formed by ethyl acetate, the filtrates are concentrated to dryness. The residue is taken up in ethyl acetate and the solution obtained is washed with 3×10 cm³ of 2N hydrochloric acid, with 3×10 cm³ of 10% sodium carbonate, then with water (2×10 cm³). After drying over anhydrous sodium sulfate and concentration, 1.1 g of a white solid are obtained (yield 75%) which are recrystallized in a dichloromethane/hexane mixture. The melting point of the solid obtained is 185° C.

Step 3

Preparation of
N-(4-cyanophenylcarbamoyl)-L-aspartyl-L-alanine
methyl ester 0.65 g (1.4 mmol) of the compound previously obtained are dissolved in 30 cm³ of methanol is the presence of 0.1 g of catalyst such as palladium on active charcoal (10%). The solution is subjected to catalytic hydrogenation under low pressure for 4 hours at 20° C. The catalyst is filtered and the solution is evaporated to dryness.

A crude compound in the form of an amorphous white powder is obtained of which the melting point is 129° C.–130° C. This compound possesses a sweet taste equivalent to 400 times that of sucrose.

EXAMPLE 2

Synthesis of
N-(4-nitrophenylcarbamoyl)-L-aspartyl-L-norvaline
methyl ester (compound No. 13 of Table I)

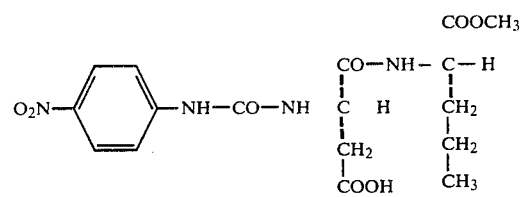

Step 1

Preparation of N-(4-nitrophenylcarbamoyl)-L-aspartic acid 4.56 g (0.0568 mol) of L-aspartic acid are dissolved in water by addition of sodium hydroxide until a pH close to 10 is obtained. A solution of 10 g (0.0568 mol) of 4-nitrophenyl isocyanate in 50 cm³ of benzene is then added at room temperature. The solution is stirred vigorously for two hours whilst maintaining the pH at around 10 by successive addition of a concentrated sodium hydroxide solution. The weak precipitate formed is eliminated by filtration and the filtrate is washed with 3×50 cm³ of ethyl ether. The aqueous phase is then acidified and extracted with ethyl acetate, which makes it possible to obtain, after drying over anhydrous sodium sulfate and after concentration, 13.4 g (yield 76%) of a yellow solid of which the melting point is 118°–120° C.

Step 2

Preparation of the anhydride of
N-(4-nitrophenylcarbamoyl)-L-aspartic acid 16 g (0.16 mol) of acetic anhydride are poured over 20 g (0.067 mol) of N-(4-nitrophenylcarbamoyl)-L-aspartic acid and the paste obtained is stirred for 10 minutes at 20° C., then for 30 minutes at reflux. The volume of the solution obtained is reduced by concentration in vacuo and anhydrous ethyl ether is added which causes the anhydride formed to precipitate. 18 g of a solid are thus obtained (yield 95%) of which the melting point is 202°–204° C.

Step 3

Preparation of
N-(4-nitrophenylcarbamoyl)-L-aspartyl-L-norvaline
methyl ester 1.05 g (3.6 mmol) of anhydride of N-(4-nitrophenylcarbamoyl)-L-aspartic acid are dissolved in 20 cm³ of ethyl acetate, then 0.47 g (3.6 mmol) of L-norvaline methyl ester are added. The solution is then maintained at 30° C. for three days. The reaction mixture is washed with 3×10 cm³ of 1N hydrochloric acid then is dried over anhydrous sodium sulfate before concentration to dryness. The product obtained is purified by dissolution in a basic medium followed by a precipitation by an N hydrochloric acid solution until a pH of 4.5 is achieved. 0.6 g of a crude compound thus purified is obtained in the form of an amorphous powder (yield 35%) of which the melting point is 220°–222° C. This compound possesses a sweet taste equivalent to 2500 times that of sucrose.

EXAMPLE 3

Synthesis of N-(4-nitrophenylcarbamoyl)-L-aspartyl-L-norleucine methyl ester (compound No. 14 of Table I)

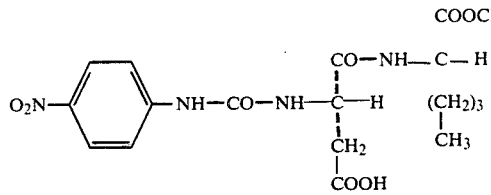

Step 1

Preparation of N-(benzyloxycarbonyl)-β-benzylester-L-aspartyl-L-norleucine methyl ester From 3 g (8.4 mmol) of N-(benzyloxycarbonyl)-β-benzylester-L-aspartic acid and from 1.35 g (8.4 mmol) of L-norleucine methyl ester, and in accordance with the process of Example 1 (Step 2), 3.2 g (yield 80%) of a solid of which the melting point is 85° C. are obtained.

Step 2

Preparation of L-aspartyl-L-norleucine methyl ester

The compound previously obtained is dissolved in 30 cm³ of methanol in the presence of 0.2 g of catalyst such as palladium on active charcoal (10%) and the solution is subjected to catalytic hydrogenation under weak pressure for 4 hours at 20° C. After filtration of the solution and concentration, 1.65 g of a white solid are obtained after trituration in ethyl ether.

Step 3

Preparation of N-(4-nitrophenylcarbamoyl)-L-aspartyl-L-norleucine methyl ester 0.51 g (1.9 mmol) of L-aspartyl-L-norleucine methyl ester are dissolved in 20 cm³ of water and some cm³ of a concentrated solution of sodium carbonate are added to bring the pH of the solution to 9–10. 0.6 g (3.8 mmol) of 4-nitrophenyl isocyanate dissolved in 5 cm³ of benzene are added at room temperature and with very strong stirring. After two hours of contact, the precipitate formed is filtered and the aqueous filtrate is washed with 3×15 cm³ of ethyl ether before its volume is reduced in vacuo by half. The solution is acidified by an N hydrochloric acid solution, until a pH of 4.5 is achieved, then filtered and the precipitate formed is washed with some cm³ of water. 0.7 g of a crude product is obtained in the form of an amorphous powder (yield 84%) of which the melting point is 204°–205° C.

This compound possesses an intensely sweet taste equivalent to 13,000–14,000 times that of sucrose.

EXAMPLE 4

Synthesis of N-(4-cyanophenylcarbamoyl)-L-aspartyl-L-phenyl alanine methyl ester (compound No. 6 of Table I)

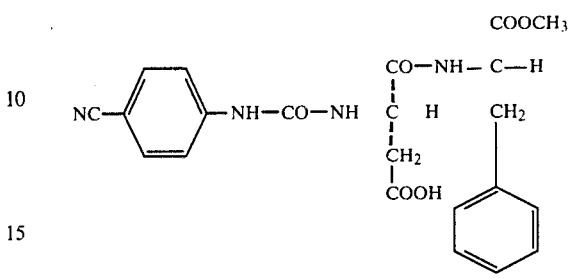

To a solution of 25 cm³ of water containing 1 g (3.39 mmol) of L-aspartyl-L-phenylalanine methyl ester and 0.21 g (1.98 mmol) of anhydrous sodium carbonate, is added a solution of 0.49 g (3.40 mol) of 4-cyanophenyl isocyanate dissolved in 10 cm³ of benzene.

A vigorous stirring is maintained for 15 minutes at room temperature before extracting the mixture with 3×20 cm³ of ethyl acetate. The aqueous phase is cooled then acidified slowly by an N hydrochloric acid solution until a pH of about 4.5 is obtained. The precipitate formed is filtered, washed with three fractions of 5 cm³ of cold water, then dried in vacuo in the presence of diphosphorus pentoxide. 1.31 g of a crude product is obtained in the form of an amorphous powder (yield 88%) the MP of which is 179°–181° C. After a recrystallization from 95% ethanol, a crystalline solid is obtained with a MP of 210° C. This compound possesses an intensely sweete taste equivalent to 10,000 times that of sucrose.

EXAMPLE 5

Synthesis of N-(4-cyanophenylthiocarbamoyl)-L-aspartyl-L-phenylalanine methyl ester (compound 10 of Table I)

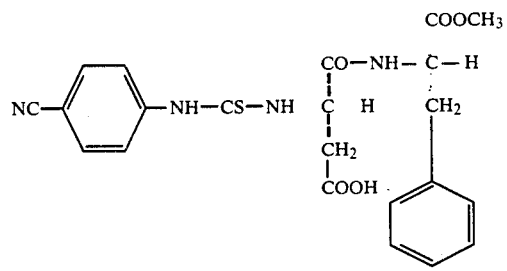

A solution of 6 g (0.051 mol) of 4-cyanoaniline in 50 cm³ of N hydrochloric acid is poured drop by drop into a suspension of 6.5 g (0.056 mol) of thiophosgene in 100 cm³ of water. The reaction medium is vigorously stirred for two hours at room temperature. The precipitate formed is filtered, washed with three fractions of 10 cm³ of water, then dried in vacuo in the presence of phosphorus pentoxide. The substance is recrystallized from a mixture of hexane and carbon tetrachloride. 7.2 g of 4-cyanophenyl isothiocyanate are obtained (yield 85%) of which the melting point is 117°–118° C.

To a solution of 25 cm³ of water containing 1 g (3.39 mmol) of L-aspartyl-L-phenylalanine methyl ester and 0.21 g (1.98 mmol) of anhydrous sodium carbonate are added 0.55 g (3.40 mmol) of 4-cyanophenyl isothiocyanate dissolved in 10 cm³ of ethanol. The solution is vigorously stirred for two hours at room temperature. After concentration by evaporation in vacuo, the aqueous solution is washed by three fractions of 20 cm³ of ethyl acetate.

After cooling, the product is acidified slowly by N hydrochloric acid until a pH of about 4.5 is obtained. The precipitate is filtered, washed with three fractions of 5 cm³ of cold water, then dried in vacuo in the presence of phosphorus pentoxide. 1 g of a crude product is achieved in the form of an amorphous powder (yield 65%) of which the melting point is 172°–173° C. This compound possesses a very intense sweet taste equivalent to 50,000 times that of sucrose.

As has been ascertained, the sweetening power of the synthetic compounds according to the invention may be of the order to ten thousand to fifty thousand, i.e. fifty to three hundred times that of the best compounds at present available on the market.

This sweetening power is assessed in the following manner.

ASSESSMENT OF THE SWEETENING POWER

The aqueous solutions of the compounds were tasted by a trained panel and compared with control solutions of sucrose. These standard solutions were chosen to be at concentrations included between 2 and 10% i.e. at concentrations corresponding to those used in normal use situations. However, a standard solution at 2% (0.058 mol/l) of sucrose was preferably used for all sensorial assessments; at that concentration, the sweet taste of the solution remains discernible by all the tasters and allows comparisons more precise than those obtained with solutions of sucrose of higher concentrations.

The sweetening power is assessed by making the molar or weight ratio, at "isosweetness" (i.e. at identical sweet tastes), between the standard solution of sucrose and the solution of the compound.

This property of the compounds of the invention of being able to communicate their intensely sweet taste to the products with which they are associated, may be illustrated by the following examples.

Test 1

A solution of 0.5 milligram of N-(4-nitrophenylthiocarbamoyl)-L-aspartyl-L-phenylalanine methyl ester (compound 11 of Table I) in a liter of water is prepared.

During the organoleptic tests, it is observed that this solution presents a sweet taste equivalent to that of a 2% sucrose solution, which corresponds to a sweetening power of 55,000 times that of sucrose on a molar basis (40,000 on a weight basis). It is observed that this same compound, in comparison with standard solutions of sucrose at 5% and 10%, possesses a sweetening power respectively of 38,000 and 23,000 (or 28,500 and 17,000 on a weight basis). The sweetening power of the compound compared with a 1% solution of sucrose (thus corresponding to a concentration slightly greater than that of the threshold of perception of the sweet taste) is 70,000 on a molar basis and 52,500 on a weight basis.

Test 2

Tea is prepared by infusing tea leaves, or coffee is prepared by dissolving 26 g of instant coffee, in a liter of water. It is observed that 100 cm³ of these solutions, sweetened with 0.5 milligram of N-(4-cyanophenylcarbamoyl)-L-aspartyl-L-phenylalanine methyl ester (compound 6 of Table I), cannot be differentiated from the same solutions of tea or coffee containing 5 g of sucrose. The sweetening power of the compound is in this case 12,800 on a molar basis comparatively to a 5% sucrose solution (or 10,000 on a weight basis). The same effect is observed by replacing the sucrose by 20 mg of aspartame. In this case, the compound is 60 times sweeter than aspartame on a molar basis and 40 times on a weight basis.

Test 3

The sweetness of some compounds of the invention corresponding to general formula (I) was assessed comparatively to 2% sucrose; the values are given in relative value on a molar basis in Table I, in which X, A, B, Y, Z designate the radicals of general formula I and mp (C.°) the melting point of the crude product directly obtained by precipitation from the water; for all compounds in Table I radical R of the general formula corresponds always to hydrogen atom and value of n is always one.

By way of comparison, the sweetening powers of some products which are known or marketed at the present time, measured by the same method, are given in Table II.

TABLE II

| Compound | Sweetness power (compared with sucrose between 2 and 10%) |
|---|---|
| Xylitol | 1.1 |
| Sodium cyclamate | 30–50 |
| Glycyrrhizin | 50 |
| Acesulfam-K | 100–130 |
| Aspartame | 100–200 |
| Saccharin | 200–400 |

TABLE I

| Compound No. | X in 4 position | A | B | Y | Z | mp (C.°) | Sweetness (Sucrose = 1) |
|---|---|---|---|---|---|---|---|
| 1 | F | O | COOH | COOCH₃ | CH₂C₆H₅ | 183–184 | 500 |
| 2 | CH₃CO | O | COOH | COOCH₃ | CH₂C₆H₅ | 156–158 | 2,200 |
| 3 | CH₃OCO | O | COOH | COOCH₃ | CH₂C₆H₅ | 183–184 | 3,800 |
| 4 | C₂H₅OCO | O | COOH | COOCH₃ | CH₂C₆H₅ | 188–189 | 2,000 |
| 5 | CH₃SO₂ | O | COOH | COOCH₃ | CH₂C₆H₅ | 133–135 | 2,100 |
| 6 | NC | O | COOH | COOCH₃ | CH₂C₆H₅ | 179–181 | 10,000 |
| 7 | O₂N | O | COOH | COOCH₃ | CH₂C₆H₅ | 196–198 | 14,000 |
| 8 | CH₃OCO | S | COOH | COOCH₃ | CH₂C₆H₅ | 93–94 | 27,000 |
| 9 | C₂H₅OCO | S | COOH | COOCH₃ | CH₂C₆H₅ | 99–100 | 13,000 |
| 10 | NC | S | COOH | COOCH₃ | CH₂C₆H₅ | 172–173 | 50,000 |
| 11 | O₂N | S | COOH | COOCH₃ | CH₂C₆H₅ | 146–147 | 55,000 |
| 12 | NC | O | COOH | COOCH₃ | CH₃ | 129–130 | 400 |
| 13 | O₂N | O | COOH | COOCH₃ | C₃H₇ | 220–222 | 2,500 |
| 14 | O₂N | O | COOH | COOCH₃ | C₄H₉ | 204–205 | 14,000 |
| 15 | NC | O | COOH | COOCH₃ | C₆H₅ | 194–197 | 10,000 |

TABLE I-continued

| Compound No. | X in 4 position | A | B | Y | Z | mp (C.°) | Sweetness (Sucrose = 1) |
|---|---|---|---|---|---|---|---|
| 16 | $O_2N$ | O | COOH | $COOCH_3$ | $C_6H_{11}$ | 203–205 | 8,000 |
| 17 | $O_2N$ | O | COOH | $COOCH_3$ | $CH_2C_6H_{11}$ | 178–180 | 5,500 |
| 18 | $O_2N$ | O | COOH | $COOCH_3$ | $CH_2OC(CH_3)_3$ | 196–198 | 3,500 |
| 19 | $O_2N$ | O | COOH | $COOCH_3$ | $COOCH_3$ | 202–203 | 13,000 |
| 20 | NC | O | COOH | $COOCH_3$ | $CF_3$ | 196–197 | 2,500 |
| 21 | $O_2N$ | O | COOH | $COOC_2H_5$ | $COOC_2H_5$ | 181–182 | 15,000 |
| 22 | $O_2N$ | O | COOH | $CH_3$ | $COOCH_3$ | 175–177 | 4,500 |
| 23 | $O_2N$ | O | COOH | $CH_3$ | $COOC_2H_5$ | 190–193 | 7,000 |
| 24 | $O_2N$ | O | COOH | $CH_3$ | $COOC_3H_7$ | 174–177 | 9,000 |
| 25 | $O_2N$ | O | COOH | $CH_3$ | $CONHC_3H_7$ | 204–207 | 300 |
| 26 | NC | O | COOH | $CH_3$ | $C_6H_5$ | 204–206 | 1,700 |
| 27 | NC | S | COOH | $CH_3$ | $C_6H_5$ | 88–90 | 3,500 |
| 28 | NC | O | COOH | $CH_3$ | $(CH_2)_2CH(CH_3)_2$ | 173–175 | 2,800 |
| 29 | NC | S | COOH | $CH_3$ | $(CH_2)_2CH(CH_3)_2$ | 125–126 | 9,000 |
| 30 | $O_2N$ | O | COOH | $CH_2OH$ | $COOCH_3$ | 175–179 | 1,700 |
| 31 | NC | O | COOH | $CH_2OH$ | $COOC_3H_7$ | 170–172 | 2,500 |
| 32 | NC | O | COOH | $CH_2OH$ | $COOCH(CH_3)_2$ | 173–175 | 1,700 |

As has already been stated, the compounds according to the invention possess a pleasant sweet taste comparable to that of sucrose.

The sweetening power of these compounds varies, as for all sweetening agents, depending on the concentration of the solution of sucrose used as reference. For example, compound 11 of Table I possesses a sweetening power of 55,000 with respect to a 2% sucrose solution, of 38,000 with respect to a 5% sucrose solution and 23,000 with respect to a 10% sucrose solution. The concentrations of sucrose included between 2 and 10% are those frequently used in normal use situations.

The sweetness power of these compounds also varies, as for the other sweeteners, depending on the nature of the product to be sweetened.

The compounds according to the invention are generally provided in solid form and, in this state, they are stable for several months under the normal conditions of storage.

In aqueous solution at 25° and at pH=4-7, the stability of these products is compatible with the uses envisaged.

The solubility of these compounds in water is average, but it proves to be sufficient being given the very small quantity of product necessary for obtaining a strong sweetening power. The solubility of these compounds may be much improved by using them in the form of salt, such as for example in the form of sodium or potassium salt.

Furthermore, the novel synthetic sweeteners according to the invention present numerous advantages over the products marketed at present, particularly over aspartame. For example:

a sweetening power on average from 40 to 300 times greater than aspartame, which is surprising and was totally unforeseeable;

excellent organoleptic properties;

a toxicity which may be compatible with the applications envisaged, since the products according to the invention must be used on average at concentrations forty to three hundred times lower than aspartame;

due to the small concentrations thus used, the secondary risks due to an excessive consumption of amino acids, and particularly of L-phenylalanine (which is contra-indicated for persons suffering from phenylketonuria) are much reduced;

likewise due to the small concentrations thus used, these products present a negligible calorie content, hence the possibility of using them in various diets;

due to the absence of a free amino group, the compounds according to the invention do not present the drawback of instability due to an intramolecular cyclization into diketopiperazinic derivative, as is the case for aspartame;

the compounds of the invention present an important economical advantage due to the fact that small quantities of product are necessary for sweetening a preparation, this reducing their cost of use accordingly;

these products do not cause caries, hence the advantage of using them in tooth pastes and chewing gums.

Consequently, they may be successfully used as sweetening products, particularly in low-sugar diets for diabetics, in low-calorie diets for obese or plethoric persons, as well as for any applications where a sweet taste is sought. By way of example, mention may be made of food (such as, for example, cakes and pastries, cooked dishes, jams, creams, ice-creams, products based on milk, fruit), beverages (such as, for example, fruit juices, vegetable juices, syrups, carbonated soft drinks, instantaneous drinks in powder form, coffee, tea, milk), confectionery, chewing gum. The compounds according to the invention may also be used to improve the taste of certain toilet, cosmetic and hygiene products (such as, for example, dentifrices, mouth-washes, gargles, lipsticks, masticatories), of certain pharmaceutical or veterinary preparations (to improve the taste of the preparation or to cover the unpleasant taste of certain drugs), and for animal foods.

What is claimed is:

1. A sweetening compound having the formula:

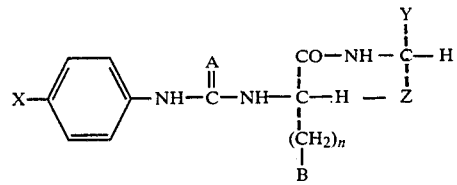

wherein X is CN, $COOC_1$-$C_3$ alkyl, $SO_2C_1$-$C_3$ alkyl, $SOC_1$-$C_3$ alkyl, $COC_1$-$C_3$ alkyl, $NO_2$, F, Cl, $SO_2NHC_1$-$C_3$ alkyl or $CONHC_1$-$C_3$ alkyl;

A is oxygen or sulfur;

n is 0 or 1;

B is COOH;

Y is $COOC_1$-$C_3$ alkyl, $CH_2OH$, $CHOHCH_3$ or $C_1$-$C_3$ alkyl; and

Z is $C_1$-$C_5$ n-alkyl, isobutyl, isopentyl, phenyl, cyclohexyl, benzyl, cyclohexylmethyl, $CH_2C_6H_4OH$, $CH_2OC_1$-$C_4$ alkyl, $CH_2SC_1$-$C_4$ alkyl, $CH_2COOC_1$-$C_4$ alkyl, $CH_2CH_2SCH_3$, $CH_2CH_2SO_2CH_3$, $COOC_1$-$C_4$ alkyl, $COOC_3$-$C_7$ cycloalkyl, $CONH$-$C_2$-$C_4$ alkyl, $CONHC_3$-$C_7$ cycloalkyl or $CONHCH_2COOCH_3$.

2. The sweetening compound of claim 1, wherein

X is CN, $COOCH_3$, $SO_2CH_3$, $NO_2$ or $SO_2NHCH_3$;

A is oxygen;

n is 1;

Y is $COOCH_3$, $CH_2OH$ or $CH_3$; and

Z is benzyl, cyclohexylmethyl, phenyl, cyclohexyl, pentyl, isopentyl, butyl, isobutyl, propylamide, dicyclopropylcarbinylamide or t-butylcyclopropylcarbinylamide.

3. The sweetening compound of claim 1, having the formula:

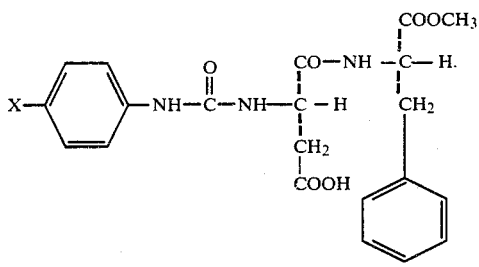

4. The sweetening compound of claim 2, having the formula:

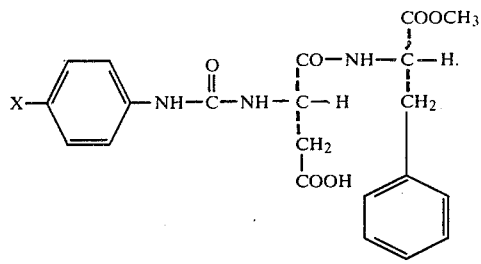

5. The sweetening compound of claim 1, having the formula:

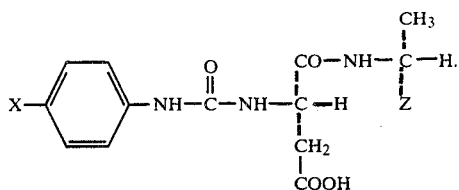

6. The sweetening compound of claim 2, having the formula:

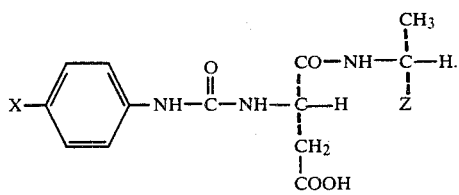

7. A sweetening composition comprising an effective amount of the sweetening compound of claim 1 and a carrier.

8. A sweetening composition comprising an effective amount of the sweetening compound of claim 2 and a carrier.

9. A sweetening composition comprising an effective amount of the sweetening compound of claim 3 and a carrier.

10. A sweetening composition comprising an effective amount of the sweetening compound of claim 4 and a carrier.

* * * * *

UNITED STATES PATENT AND TRADEMARK OFFICE
CERTIFICATE OF CORRECTION

PATENT NO. : 4,645,678
DATED : February 24, 1987
INVENTOR(S) : NOFRE et al

It is certified that error appears in the above-identified patent and that said Letters Patent is hereby corrected as shown below:

In "OTHER PUBLICATIONS", item 2, change "Tini" to --Tinti--.

In "OTHER PUBLICATIONS", item 4, change "Ariyashi" to --Ariyoshi--.

In the "ABSTRACT", change the structural formula to read as follows:

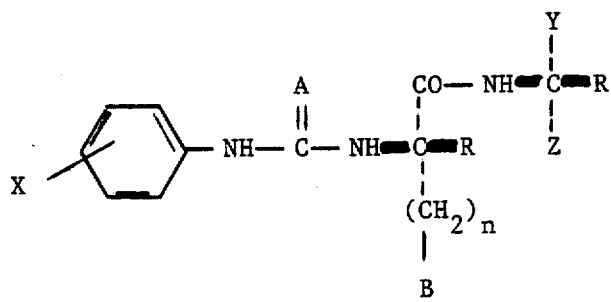

Column 2, line 5, change the structural formula to read as follows:

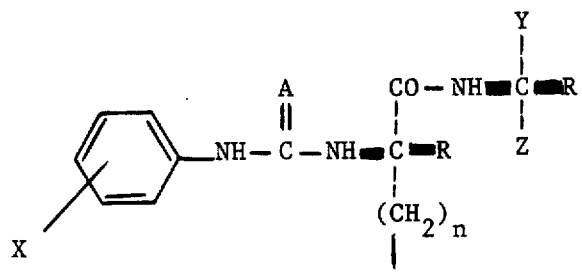

Column 2, line 64, change "CONHCHR'-" to --CONHCHR"- --.

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 3, line 30, change the structural formula to read as follows:

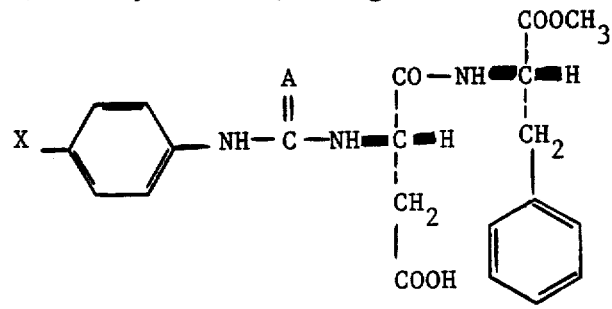

Column 3, line 45, change the structural formula to read as follows:

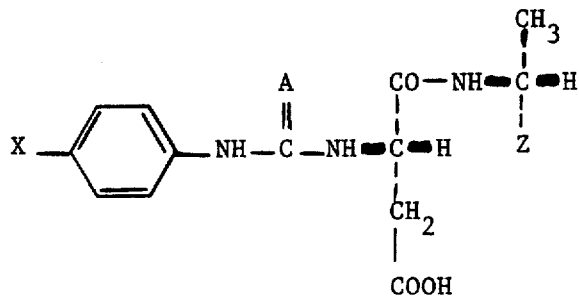

UNITED STATES PATENT AND TRADEMARK OFFICE
CERTIFICATE OF CORRECTION

PATENT NO. : 4,645,678

DATED : February 24, 1987

INVENTOR(S) : NOFRE et al.

It is certified that error appears in the above-identified patent and that said Letters Patent is hereby corrected as shown below:

Column 3, line 55, change the structural formula to read as follows:

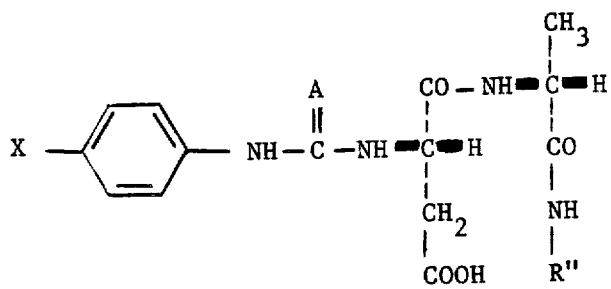

Column 4, line 5, change the structural formula to read as follows:

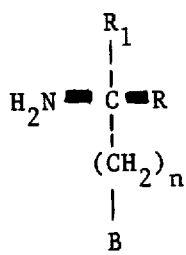

Column 4, line 15, change the structural formula to read as follows:

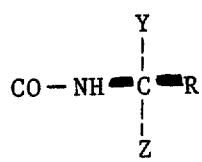

UNITED STATES PATENT AND TRADEMARK OFFICE
CERTIFICATE OF CORRECTION

PATENT NO. : 4,645,678
DATED : February 24, 1987
INVENTOR(S) : NOFRE et al

It is certified that error appears in the above-identified patent and that said Letters Patent is hereby corrected as shown below:

Column 4, line 35, change the structural formula to read as follows:

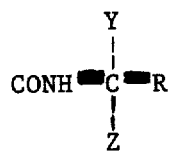

Column 4, line 45, change the structural formula to read as follows:

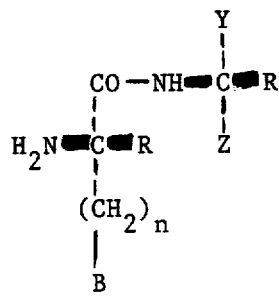

Column 4, line 60, change the structural formula to read as follows:

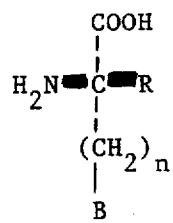

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 5, line 5, change the structural formula to read as follows:

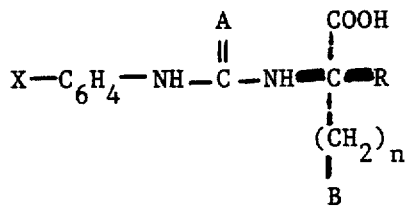

Column 5, line 15, change the structural formula to read as follows:

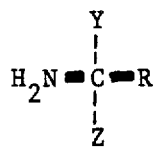

Column 6, line 5, change the structural formula to read as follows:

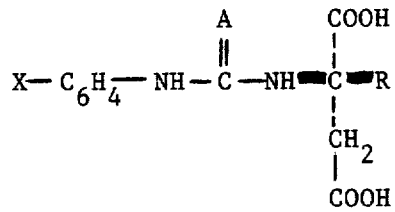

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 6, line 20, change the structural formula to read as follows:

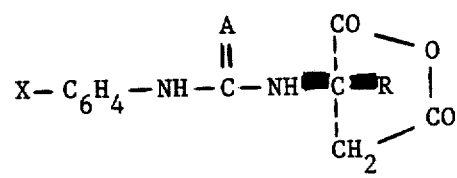

UNITED STATES PATENT AND TRADEMARK OFFICE
CERTIFICATE OF CORRECTION

PATENT NO. : 4,645,678
DATED : February 24, 1987
INVENTOR(S) : NOFRE et al

It is certified that error appears in the above-identified patent and that said Letters Patent is hereby corrected as shown below:

Column 7, line 10, change the structural formula to read as follows:

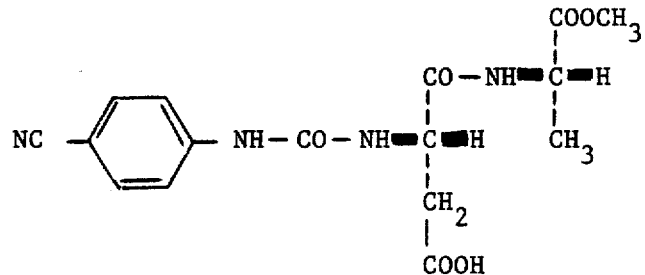

Column 7, line 36, change "benzyl-ester" to --benzylester--.

Column 8, line 15, change the structural formula to read as follows:

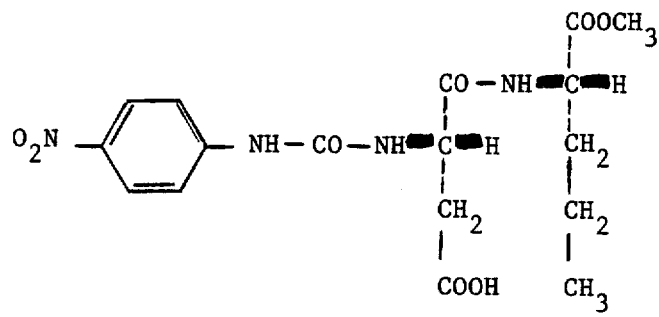

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 9, line 20, change the structural formula to read as follows:

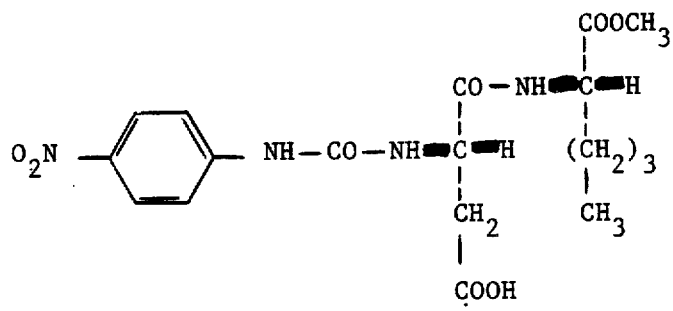

Column 10, line 10, change the structural formula to read as follows:

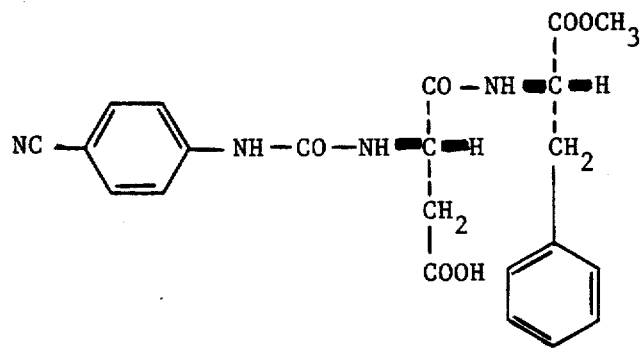

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 10, line 45, change the structural formula to read as follows:

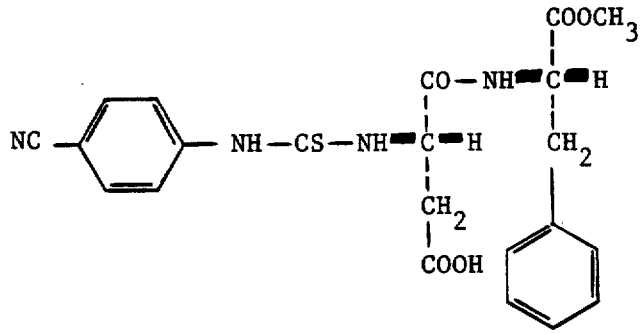

Column 14, line 55, change the structural formula to read as follows:

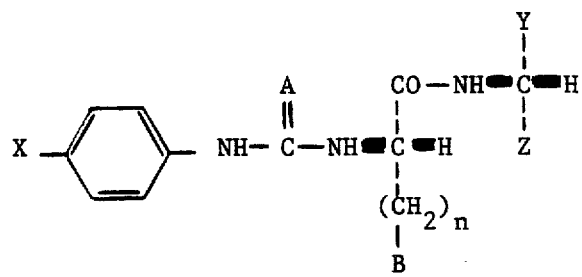

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 15, in Claim 3, please change the structural formula to read as follows:

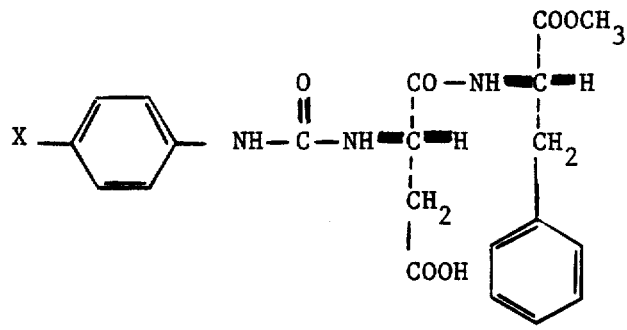

Column 16, in Claim 4, please change the structural formula to read as follows:

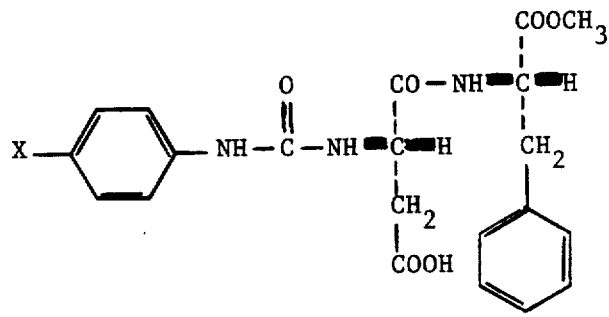

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 16, in Claim 5, change the structural formula to read as follows:

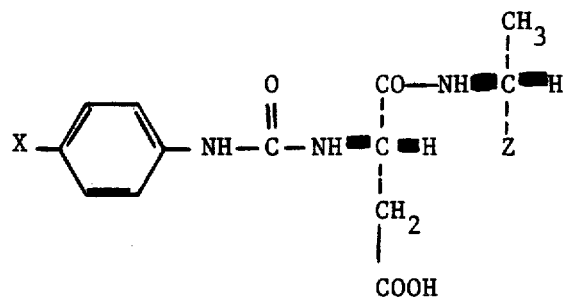

UNITED STATES PATENT AND TRADEMARK OFFICE
CERTIFICATE OF CORRECTION

PATENT NO. : 4,645,678

DATED : February 24, 1987

INVENTOR(S) : NOFRE et al

It is certified that error appears in the above-identified patent and that said Letters Patent is hereby corrected as shown below:

Column 16, in Claim 6, change the structural formula to read as follows:

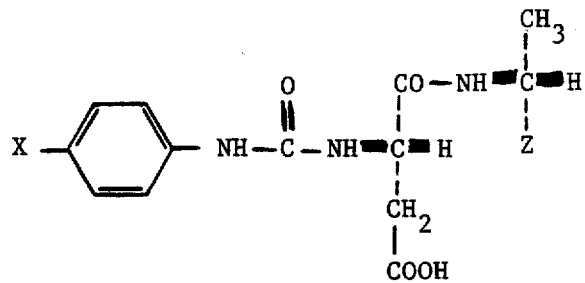

Signed and Sealed this

Twentieth Day of October, 1987

Attest:

DONALD J. QUIGG

Attesting Officer

Commissioner of Patents and Trademarks